(12) United States Patent
Vanermen et al.

(10) Patent No.: US 7,993,395 B2
(45) Date of Patent: Aug. 9, 2011

(54) SET OF ANNULOPLASTY DEVICES WITH VARYING ANTERIOR-POSTERIOR RATIOS AND RELATED METHODS

(75) Inventors: Hugo Vanermen, Knokke (BE); Timothy R. Ryan, Shorewood, MN (US); Michael A. Gloss, Minneapolis, MN (US); Stephen Kuehn, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 36 days.

(21) Appl. No.: 12/357,551

(22) Filed: Jan. 22, 2009

(65) Prior Publication Data

US 2009/0264996 A1   Oct. 22, 2009

Related U.S. Application Data

(60) Provisional application No. 61/062,412, filed on Jan. 25, 2008.

(51) Int. Cl.
*A61F 2/24* (2006.01)
(52) U.S. Cl. ..................... 623/2.36; 623/2.37
(58) Field of Classification Search .......... 623/2.1–2.37
See application file for complete search history.

(56) References Cited

U.S. PATENT DOCUMENTS

| | | |
|---|---|---|
| 3,656,185 A | 4/1972 | Carpentier |
| 3,966,401 A | 6/1976 | Hancock et al. |
| 4,050,893 A | 9/1977 | Hancock et al. |
| 4,055,861 A | 11/1977 | Carpentier et al. |
| 4,164,046 A | 8/1979 | Cooley |
| 4,182,446 A | 1/1980 | Penny |
| 4,917,698 A | 4/1990 | Carpentier et al. |
| 5,011,481 A | 4/1991 | Myers et al. |
| 5,041,130 A | 8/1991 | Cosgrove et al. |
| 5,061,277 A | 10/1991 | Carpentier et al. |
| 5,104,407 A | 4/1992 | Lam et al. |
| 5,201,880 A | 4/1993 | Wright et al. |
| 5,258,021 A | 11/1993 | Duran |
| 5,290,300 A | 3/1994 | Cosgrove et al. |

(Continued)

FOREIGN PATENT DOCUMENTS

EP    0 257 874    3/1988

(Continued)

OTHER PUBLICATIONS

Ahmadi, A., et al., "Hemodynamic Changes Following Experimental Production and Correction of Acute Mitral Regurgitation With an Adjustable Ring Prosthesis," The Thoracic and Cardiovascular Surgeon, vol. 36, No. 6, pp. 313-319 (1988).

(Continued)

*Primary Examiner* — David Isabella
*Assistant Examiner* — Seema Swaminathan

(57) ABSTRACT

Described is a set of at least two annuloplasty devices having a particular size that corresponds to an inter-trigonal or inter-commissural distance of a heart valve annulus, wherein the at least two annuloplasty devices have different anterior-posterior ratios. Also, described is a kit for annuloplasty repair of a heart valve annulus including a plurality of annuloplasty devices each comprising one of a plurality of different sizes, wherein the different sizes each correspond to a different inter-trigonal or inter-commissural distance of a heart valve annulus, and for each of the plurality of different sizes there are at least two devices each having the same size but having different anterior-posterior ratios. Additionally, a method of choosing an annuloplasty device for implantation in a valve annulus is described.

9 Claims, 7 Drawing Sheets

U.S. PATENT DOCUMENTS

| | | | |
|---|---|---|---|
| 5,306,296 | A | 4/1994 | Wright et al. |
| 5,350,420 | A | 9/1994 | Cosgrove et al. |
| 5,376,112 | A | 12/1994 | Duran |
| 5,496,336 | A | 3/1996 | Cosgrove et al. |
| 5,522,884 | A | 6/1996 | Wright |
| 5,593,424 | A | 1/1997 | Northrup, III |
| 5,601,576 | A | 2/1997 | Cosgrove |
| 5,607,471 | A | 3/1997 | Seguin et al. |
| 5,669,919 | A | 9/1997 | Sanders et al. |
| 5,674,279 | A | 10/1997 | Wright et al. |
| 5,674,280 | A | 10/1997 | Davidson et al. |
| 5,683,402 | A | 11/1997 | Cosgrove et al. |
| 5,716,397 | A | 2/1998 | Myers |
| 5,824,066 | A | 10/1998 | Gross |
| 5,860,992 | A | 1/1999 | Daniel et al. |
| 5,972,030 | A | 10/1999 | Garrison et al. |
| 6,102,945 | A | 8/2000 | Campbell |
| 6,143,024 | A * | 11/2000 | Campbell et al. ............ 623/2.36 |
| 6,159,240 | A | 12/2000 | Sparer et al. |
| 6,165,183 | A | 12/2000 | Kuehn et al. |
| 6,174,332 | B1 | 1/2001 | Loch et al. |
| 6,183,512 | B1 | 2/2001 | Howance, Jr. et al. |
| 6,187,040 | B1 | 2/2001 | Wright |
| 6,217,610 | B1 | 4/2001 | Carpentier et al. |
| 6,231,602 | B1 | 5/2001 | Carpentier et al. |
| 6,283,993 | B1 | 9/2001 | Cosgrove et al. |
| 6,319,280 | B1 | 11/2001 | Schoon |
| 6,368,348 | B1 | 4/2002 | Gabbay |
| 6,406,492 | B1 | 6/2002 | Lytle |
| 6,416,548 | B2 | 7/2002 | Chin et al. |
| 6,416,549 | B1 | 7/2002 | Chin et al. |
| 6,528,107 | B2 | 3/2003 | Chin et al. |
| 6,565,603 | B2 | 5/2003 | Cox |
| 6,602,289 | B1 | 8/2003 | Colvin et al. |
| 6,695,866 | B1 | 2/2004 | Kuehn et al. |
| 6,726,717 | B2 | 4/2004 | Alfieri et al. |
| 6,749,630 | B2 | 6/2004 | McCarthy et al. |
| 6,786,924 | B2 | 9/2004 | Ryan et al. |
| 6,797,002 | B2 | 9/2004 | Spence et al. |
| 6,805,710 | B2 | 10/2004 | Bolling et al. |
| 6,858,039 | B2 | 2/2005 | McCarthy |
| 6,908,482 | B2 | 6/2005 | McCarthy et al. |
| 6,955,689 | B2 | 10/2005 | Ryan et al. |
| 7,294,148 | B2 | 11/2007 | McCarthy |
| 7,329,280 | B2 | 2/2008 | Bolling et al. |
| 7,367,991 | B2 | 5/2008 | McCarthy et al. |
| 7,371,259 | B2 | 5/2008 | Ryan et al. |
| 7,377,940 | B2 | 5/2008 | Ryan et al. |
| 7,575,595 | B2 | 8/2009 | Ingle et al. |
| 7,608,103 | B2 | 10/2009 | McCarthy |
| 7,674,286 | B2 | 3/2010 | Alfieri et al. |
| 2001/0010018 | A1 | 7/2001 | Cosgrove et al. |
| 2001/0021874 | A1 | 9/2001 | Carpentier et al. |
| 2001/0034551 | A1 | 10/2001 | Cox |
| 2001/0041933 | A1 | 11/2001 | Thoma |
| 2001/0049557 | A1 | 12/2001 | Chinn et al. |
| 2001/0049558 | A1 | 12/2001 | Liddicoat et al. |
| 2002/0129820 | A1 | 9/2002 | Ryan et al. |
| 2002/0169503 | A1 | 11/2002 | Lytle |
| 2002/0173844 | A1 | 11/2002 | Alfieri et al. |
| 2003/0045929 | A1 | 3/2003 | McCarthy et al. |
| 2003/0093148 | A1 | 5/2003 | Bolling et al. |
| 2003/0125715 | A1 | 7/2003 | Kuehn et al. |
| 2004/0006384 | A1 | 1/2004 | McCarthy |
| 2004/0088047 | A1 | 5/2004 | Spence et al. |
| 2005/0004665 | A1 | 1/2005 | Aklog |
| 2005/0049698 | A1 | 3/2005 | Bolling et al. |
| 2005/0131533 | A1 | 6/2005 | Alfieri et al. |
| 2005/0182487 | A1 | 8/2005 | McCarthy et al. |
| 2005/0256567 | A1 | 11/2005 | Lim et al. |
| 2005/0256568 | A1* | 11/2005 | Lim et al. ...................... 623/2.36 |
| 2005/0256569 | A1 | 11/2005 | Lim et al. |
| 2005/0267572 | A1 | 12/2005 | Schoon et al. |
| 2006/0025856 | A1 | 2/2006 | Ryan et al. |
| 2006/0129236 | A1 | 6/2006 | McCarthy |
| 2007/0100441 | A1 | 5/2007 | Kron et al. |
| 2007/0156234 | A1 | 7/2007 | Adzich et al. |
| 2008/0058924 | A1 | 3/2008 | Ingle et al. |
| 2009/0157176 | A1 | 6/2009 | Carpentier et al. |
| 2009/0177276 | A1 | 7/2009 | Carpentier et al. |
| 2009/0192605 | A1 | 7/2009 | Gloss et al. |
| 2009/0192606 | A1 | 7/2009 | Gloss et al. |
| 2009/0287303 | A1 | 11/2009 | Carpentier |
| 2010/0030329 | A1* | 2/2010 | Frater .......................... 623/2.36 |

FOREIGN PATENT DOCUMENTS

| | | |
|---|---|---|
| EP | 0 338 994 | 10/1989 |
| EP | 0 495 417 | 7/1992 |
| EP | 1 034 753 | 2/2005 |
| WO | 91/17721 | 11/1991 |
| WO | 99/04730 | 2/1999 |
| WO | 99/29269 | 6/1999 |
| WO | 99/49816 | 10/1999 |
| WO | 00/23007 | 4/2000 |
| WO | 00/59408 | 10/2000 |
| WO | 00/62715 | 10/2000 |
| WO | 00/74603 | 12/2000 |
| WO | 02/074197 | 9/2002 |
| WO | 03/020178 | 3/2003 |
| WO | 03/041617 | 5/2003 |
| WO | 03/053289 | 7/2003 |
| WO | 2007/143077 | 12/2007 |

OTHER PUBLICATIONS

Alonso-Lei, "Adjustable Annuloplasty for Tricuspid Insufficiency," The Annals of Thoracic Surgery, (1988) 46(3), pp. 368-369.

Alonso-Lej, F., "The 'dynamic' mitral ring: A new concept in treating mitral insufficiency," Recent Progress in Mitral Valve Disease, pp. 45 and 443-449 (1984).

AnnuloFlex® and AnnuloFlo® Systems, Implantation techniques for mitral and tricuspid indications, CarboMedics (2003) (24 pages).

Belcher, J.R., "The Surgical Treatment of Mitral Regurgitation," British Heart Journal, vol. 26, pp. 513-523 (1964).

Bex J.P. and Lecompte Y., "Tricuspid valve repair using a flexible linear reducer," J. Cardiac Surg., 1:151 (1986).

Bolling, "Mitral Valve Reconstruction in the Patient with Heart Failure," Heart Failure Reviews, (2001) 6, pp. 177-185.

Bolling, et al., "Surgical Alternatives for Heart Failure," The Journal of Heart and Lung Transplantation, (2001) 20(7), pp. 729-733.

Bolling, S.F., et al., "Surgery for Acquired Heart Disease," The Journal of Thoracic and Cardiovascular Surgery, vol. 109, No. 4, pp. 676-683 (1995).

Bolling, S.F., "Mitral Reconstruction in Cardiomyopathy," The Journal of Heart Valve Disease, vol. 11, Suppl. 1, pp. S26-S31 (2002).

Carpentier-Edwards® Annuloplasty Rings (3 pages) (copy can be found in the file history for U.S. Appl. No. 10/918,503).

Carpentier-Edwards Physio™ Annuloplasty Ring (3 pages) (copy can be found in the file history for U.S. Appl. No. 10/918,503).

Carpentier, A., "La Valvuloplastie Reconstitutive: Une Nouvelle Technique de Valvuloplastie Mitrale," Technique Chirugicale, No. 7, pp. 251-255 (1969).

Carpentier, A., et al., "A New Reconstructive Operation for Correction of Mitral and Tricuspid Insufficiency," The Journal of Thoracic and Cardiovascular Surgery, vol. 61, No. 1, pp. 1-13 (1971).

Carpentier A., Deloche A., Hanania G., et al., "Surgical management of acquired tricuspid valve disease," J. Thorac. Cardiovasc. Surg., 67:53 (1974).

Carpentier, A.F., et al., "The 'Physio-Ring': An Advanced Concept in Mitral Valve Annuloplasty," Ann. Thorac. Surg., vol. 60, No. 5, pp. 1177-1186 (1995).

Castells, E., et al., "Long-Term Results with the Puig Massana-Shiley Annuloplasty Ring," The Journal of Cardiovascular Surgery, Abstracts, vol. 24, No. 4, p. 387 (1983).

Chachques, J.C., et al., "Absorbable Rings for Pediatric Valvuloplasty: Preliminary Study," Supplement IV to Circulation, vol. 82, No. 5, pp. IV-82-IV-88 (1990).

Cochran, et al., "Effect of Papillary Muscle Position on Mitral Valve Function: Relationship to Homografts," Ann. Thorac. Surg, (1998) 66:SS155-61.

Cooley, D.A., et al., "Mitral Leaflet Prolapse: Surgical Treatment using a Posterior Annular Collar Prosthesis," Cardiovascular Diseases Bulletin of the Texas Heart Institute, vol. 3, No. 4, pp. 438-443 (1976).

Cooley, D.A., "Ischemic Mitral Insufficiency," Cardiac Surgery: State of the Art Reviews, vol. 6, No. 2, pp. 237-249 (1992).

Cooley, D.A., et al., "A Cost-Effective Dacron Annuloplasty Ring," The Annals of Thoracic Surgery, vol. 56, pp. 185-186 (1993).

Cosgrove, D.M., III, et al., "Initial Experience with the Cosgrove-Edwards Annuloplasty System," The Annals of Thoracic Surgery, vol. 60, pp. 499-504 (1995).

Dagum et al., "Three-dimensional geometric comparison of partial and complete flexible mitral annuloplasty rings," The J. of Thorac. and Cardiovasc. Surg., vol. 122, No. 4 (2001).

Deloche, A., et al., "Valve Repair with Carpentier Techniques," The Journal of thoracic and Cardiovascular Surgery, vol. 99, No. 6, pp. 990-1002 (1990).

Department of Health & Human Services letter and attachments regarding file K926138, Carpentier-Edwards Physio™ Annuloplasty Ring, Model 4450 Mitral, dated Jun. 22, 1993 (295 pages).

Duran, C.,M.G., et al., "Valve Repair in Rheumatic Mitral Disease," Supplement to Circulation, vol. 84, No. 5, pp. III 125-III 132 (1990).

Duran, C.G., et al., "Clinical and Hemodynamic Performance of a Totally Flexible Prosthetic Ring for Atrioventricular Valve Reconstruction," The Annals of Thoracic Surgery, vol. 22, No. 5, pp. 458-463 (1976).

Duran, C.G., "Reconstructive procedures of the Mitral Valve Including Ring Annuloplasty," Modern Technics in Surgery, 20 (1979).

Durán, C.M.G., et al., "A New Absorbable Annuloplasty Ring in the Tricuspid Position: An Experimental Study," The Thoracic and Cardiovascular Surgeon, vol. 34, No. 6, pp. 377-379 (1986).

Duran, C.G., et al., "Stability of Mitral Reconstructive Surgery at 10-12 Years for Predominantly Rheumatic Valvular Disease," Circulation Supplement I, vol. 78, No. 3, pp. I-91—I-96 (1988).

Erk, M.K., et al., "Semi-frame Mitral Annuloplasty," Cardiac Reconstructions pp. 157-163 (1989).

Erk, M.K., "Morphological and Functional Reconstruction of the Mitral Valve: A New Annuloplastic Procedure," Texas Heart Institute Journal, vol. 9, pp. 329-334 (1982).

Flachskampf, et al., "Analysis of Shape and Motion of the Mitral Annulus in Subjects With and Without Cardiomyopathy by Echocardiographic 3-Dimensional Reconstruction," Journal of the American Society of Echocardiography, (2000) 13(4), pp. 277-287.

Freed, et al., "Prevalence and Clinical Outcome of Mitral-Valve Prolapse," The New England Journal of Medicine, (1999) 341(1), pp. 1-7.

Fundarò, P., et al., "Polytetrafluoroethylene Posterior Annuloplasty for Mitral Regurgitation," The Annals of Thoracic Surgery, Correspondence, vol. 50, No. 1, pp. 165-166 (1990).

Galler M. Kronzon I, Slater J., et al., "Long-term follow-up after mitral valve reconstruction: incidence of post-operative left ventricular out flow obstruction," Circulation, 74:I-99 (1986).

Gatti, et al., "Preliminary experience in mitral valve repair using the Cosgrove-Edwards annuloplasty ring," Interact Cardiovasc Thorac Surg, (2003) 2:256-261.

Ghosh, P.K., "Mitral Annuloplasty: A Right-Side View," The Journal of Heart Valve Disease, vol. 5, pp. 286-293 (1996).

Gorman, et al., "Dynamic Three-Dimensional Imaging of the Mitral Valve and Left Ventricle by Rapid Sonomicrometry Array Localization," J Thorac Card Surg, 112(3), (1996) pp. 712-726.

Gorman, et al., "The Effect of Regional Ischemia on Mitral Valve Annular Saddle Shape," Ann Thorac Surg (2004) 77, pp. 544-548.

Gorton, M.E., et al., "Mitral Valve Repair Using a Flexible and Adjustable Annuloplasty Ring," The Annals of Thoracic Surgery, vol. 55, pp. 860-863 (1993).

Gregori, F., et al., "Mitral Valvuloplasty with a New Prosthetic Ring," Official Journal of the European Association for Cardio-thoracic Surgery, vol. 8, No. 4, pp. 168-172 (1994).

Gregori, F., Jr., et al., "Um Novo Modelo De Anel Protetico Para Pacientes Com Insuficiencia Valvar Mitral. Relato de Dois Casos," Arquivos Brasileiros de Cardiologia, vol. 50, No. 6, pp. 417-420 (1988).

Haverich, et al., "Experimental and Clinical Experiences with Double-velour Woven Dacron Prostheses," Thorac. Cardiovasc. Surgeon 34 (1986) pp. 52-53.

Hendren, W.G., et al., "Mitral Valve Repair for Ischemic Mitral Insufficiency," The Annals of Thoracic Surgery, vol. 52, pp. 1246-1252 (1991).

Henze, A., et al., "The Adjustable Half-Moon: An Alternative Device for Tricuspid Valve Annuloplasty," Scandinavian Journal of Thoracic and Cardiovascular Surgery, vol. 18, pp. 29-32 (1984).

Jimenez, et al., "Effects of a Saddle Shaped Annulus on Mitral Valve Function and Chordal Force Distribution: An In Vitro Study," Annals of Biomedical Engineering, (2003) vol. 31, pp. 1171-1181.

Kasegawa, H., et al., "Physiologic Remodeling Annuloplasty to Retain the Shape of the Anterior Leaflet: A New Concept in Mitral Valve Repair," The Journal of Heart Valve Disease, vol. 6, pp. 604-607 (1997).

Katz, N. M., "Current Surgical Treatment of Valvular Heart Disease," American Family Physician, vol. 52, No. 2, pp. 559-568 (1995).

Kaye, D.M., et al., "Feasibility and Short-Term Efficacy of Percutaneous Mitral Annular Reduction for the Therapy of Heart Failure—Induced Mitral Regurgitation," Circulation, Brief Rapid Communication, No. 108, pp. 1795-1797 (2003).

Kurosawa, H., et al., "Mitral Valve Repair by Carpentier-Edwards Physio Annuloplasty Ring," The Japanese Journal of Thoracic and Cardiovascular Surgery, vol. 47, pp. 355-360 (1999).

Lachmann, J., M.D., et al., "Mitral Ring Annuloplasty: An Incomplete Correction of Functional Mitral Regurgitation Associated with Left Ventricular Remodeling," Current Cardiology Reports, vol. 3, pp. 241-246 (2001).

Levine, R.A., et al., "The Relationship of Mitral Annular Shape to the Diagnosis of Mitral Valve Prolapse," Circulation, vol. 75, No. 4, pp. 756-767 (1987).

Levin, et al., "Three-Dimensional Echocardiographic Reconstruction of the Mitral Valve, With Implications for the Diagnosis of Mitral Valve Prolapse," Circulation, 1989; 80(3):589-598.

Martin, S.L., et al., "Echocardiographic Evaluation of Annuloplasty Rings: Comparison of Continuity Equation and Pressure Half-Time Methods," Journal of The American Society of Echocardiography, vol. 5, No. 3, p. 322 (1992).

Medtronic® Sculptor™ Annuloplasty Ring brochure, Medtronic Inc. (1993) (6 pages).

Melo, et al., "Atrioventricular Valve Repair Using Externally Adjustable Flexible Rings," The Journal of Thoracic and Cardiovascular Surgery, (1995) 110(5), pp. 1333-1337.

Miller, "Ischemic mitral regurgitation redux—To repair or to replace?" The Journal of Thoracic and Cardiovascular Surgery, (2001) 122(6), pp. 1059-62.

Morse, D., et al., "Cardiac Valve Identification Atlas and Guide," Chapter 10 in Guide to Prosthetic Cardiac Valves, edited by Dryden Morse, Robert M. Steiner, and Javier Fernandez, Springer-Verlag New York Inc. (1985).

Murphy, J.P., et al., "The Puig-Massana-Shiley Annuloplasty Ring for Mitral Valve Repair: Experience in 126 Patients," The Annals of Thoracic Surgery, vol. 43, pp. 52-58 (1987).

Ogus, T.N., et al., "Posterior Mitral Annuloplasty with an Adjustable Homemade Ring," Journal of Cardiac Surgery, vol. 17, No. 3, pp. 226-228 (2002).

Pellegrini, A., et al., "Posterior Annuloplasty in the Surgical Treatment of Mitral Insufficiency," The Journal of Heart Valve Disease, vol. 2, pp. 633-638 (1993).

Reece, I.J., et al., "Surgical Treatment of Mitral Systolic Click Syndrome: Results in 37 Patients," The Annals of Thoracic Surgery, vol. 39, No. 2, pp. 155-158 (1985).

Rubenstein, F., et al., "Alternatives in Selection of Rings for Mitral Annuloplasty," Current Opinion in Cardiology, vol. 16, No. 2, pp. 136-139 (2001).

Salati, M., et al., "Annular Remodeling with Pericardial Reinforcement: Surgical Technique and Early Results," The Journal of Heart Valve Disease, vol. 2, pp. 639-641 (1993).

Salati, M., et al., "Posterior Pericardial Annuloplasty: A Physiocological Correction?", European Journal of Cardio-Thoracic Surgery, vol. 5, pp. 226-229 (1991).

Salgo, et al., "Effect of Annular Shape on Leaflet Curvature in Reducing Mitral Leaflet Street," Circulation, 2002; 106:711-717.

Salvador, L., et al., "The Pericardium Reinforced Suture Annuloplasty: Another Tool Available for Mitral Annulus Repair," Journal of Cardiac Surgery, vol. 8, pp. 79-84 (1993).

Sato, et al., "The Biologic Fate of Dacron Double Velour Vascular Prostheses—A Clinicopathological Study," Japanese Journal of Surgery, (1989) 19(3), pp. 301-311.

Seguin, et al., "Advance in Mitral Valve Repair Using a Device Flexible in Three Dimensions," ASAIO Journal (1996), 42:M368-M371.

Shumway, S.J., et al., "A 'Designer' Annuloplasty Ring for Patients with Massive Mitral Annular Dilation," The Annals of Thoracic Surgery, vol. 46, No. 6, pp. 695-696 (1988).

Smolens, I., et al., "Current Status of Mitral Valve Reconstruction in Patients with Dilated Cardiomyopathy," Ital. Heart J., vol. 1, No. 8, pp. 517-520 (2000).

Smolens, et al., "Mitral valve repair in heart failure," The European Journal of Heart Failure, (2000) 365-371.

Tsakiris, A.G., "The psysiology of the mitral valve annulus," in The Mitral Valve-apluridisciplinary Approach, ed Kalmanson D. Publishing Sciences Group, Acton, Mass., p. 21 (1976).

Victor, S., et al., "Truly Flexible D-Shaped Autogenous Pericardial Ring for Mitral Annuloplasty," The Annals of Thoracic Surgery, vol. 56, pp. 179-180 (1993).

Vongpatanasin, W., et al., "Prosthetic Heart Valves," The New England Journal of Medicine, vol. 335, No. 6, pp. 407-416 (1996).

* cited by examiner

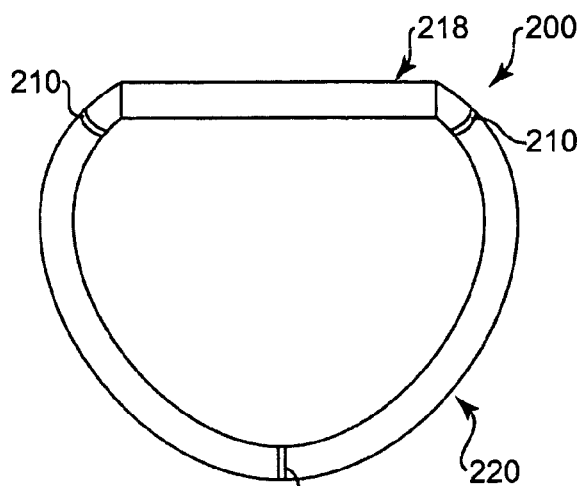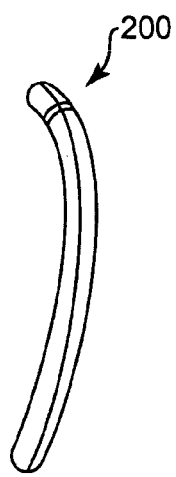
Fig. 1    Fig. 2
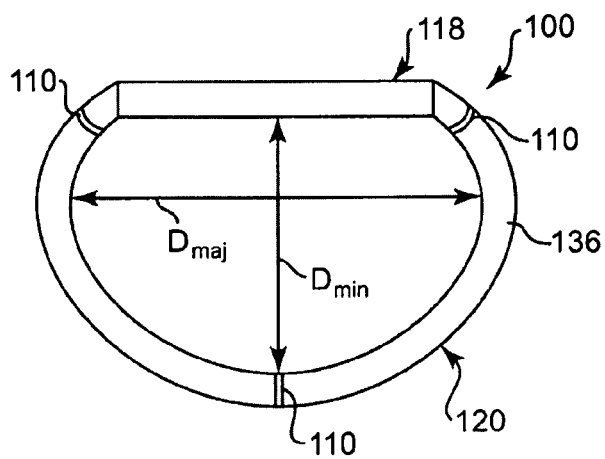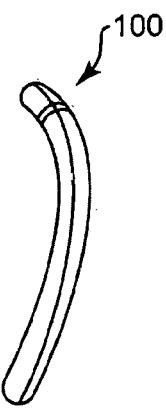
Fig. 3    Fig. 4
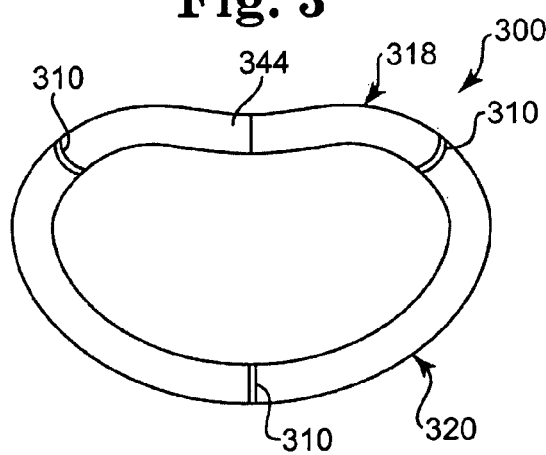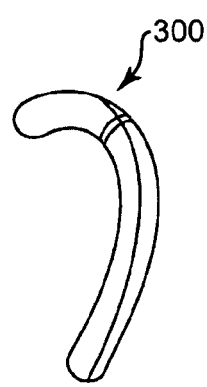
Fig. 5    Fig. 6

SET OF ANNULOPLASTY DEVICES WITH VARYING ANTERIOR-POSTERIOR RATIOS AND RELATED METHODS

PRIORITY

The present non-provisional patent application claims benefit from U.S. Provisional Patent Application having Ser. No. 61/062,412, filed on Jan. 25, 2008, by Ryan et al., and titled SYSTEM OF ANNULOPLASTY DEVICES WITH VARYING ANTERIOR-POSTERIOR RATIOS AND RELATED DEVICES AND METHODS, wherein the entirety of said provisional patent application is incorporated herein by reference.

TECHNICAL FIELD

The present invention relates generally to devices and methods for repair of heart valves, and more particularly to a set of annuloplasty devices for mitral valve repair that includes devices having varying anterior-posterior ratios to treat different pathologies.

BACKGROUND OF THE INVENTION

Heart valve disease is a widespread condition in which one or more of the valves of the heart fails to function properly. Various surgical techniques may be used to replace or repair a diseased or damaged valve. In just one way, in a valve replacement surgery, damaged leaflets of the valve are excised and the annulus is sculpted to receive a replacement valve. Another less drastic method for treating defective valves is repair or reconstruction by annuloplasty, in which the valve annulus is re-shaped and held in place by attaching a prosthetic annuloplasty repair segment or ring to an interior wall of the heart around the valve annulus. The annuloplasty ring is designed to support the functional changes that occur during the cardiac cycle; maintaining coaptation and valve integrity.

There are two atrio-ventricular valves in the heart, which include the mitral valve on the left side of the heart and the tricuspid valve on the right side of the heart. Anatomically speaking, each valve type forms or defines a valve annulus and valve leaflets; however, the mitral and tricuspid valves differ significantly in anatomy. Whereas the annulus of the mitral valve is somewhat "D" shaped, the annulus of the tricuspid valve is more nearly elliptical. Both valves can be subjected to or incur damage that requires that one or both of the valves be repaired or replaced. Annuloplasty prostheses, which can generally be categorized as either annuloplasty rings or annuloplasty bands, are employed in conjunction with valvular reconstructive surgery to assist in the correction of heart valve defects such as stenosis and valvular insufficiency.

One type of valvular insufficiency is ischemic mitral regurgitation (IMR). In IMR, the coordination of the mitral leaflets, the mitral annulus, the subvalvular apparatus and the left ventricular wall is upset in some way. There are many causes, such as congenital defects, rheumatic fever, endocarditis, etc. There is a classification system for IMR, which was developed by Carpentier. IMR is classified as either Type I, II, IIIa or IIIb, based mainly on leaflet motion.

The effects of valvular dysfunction vary, with IMR typically having more severe physiological consequences to the patient than tricuspid valve regurgitation. In either area of the heart, however, many of the defects are associated with dilation of the valve annulus. This dilation not only prevents competence of the valve but also results in distortion of the normal shape of the valve orifice. Remodeling of the annulus is therefore central to most reconstructive procedures on the valves. Clinical experience has shown that repair of the valves, when technically possible, produces better long-term results than valve replacement.

With regard to the mitral valve, many procedures have been described to correct the pathology of the valve leaflets and their associated chordae tendinae and papillary muscles. The mitral valve, in particular, is a bicuspid valve having a posterior leaflet that has an annulus insertion length that is larger than that of an anterior leaflet, which coapts or meets with the posterior leaflet. Each of the leaflets has indentations dividing them each into three segments, with the posterior leaflet having segments P1 (anterolateral), P2 (middle) and P3 (posteromedial), and the anterior leaflet having segments A1 (anterolateral), A2 (middle) and A3 (posteromedial). The part of the mitral valve annulus that is attached to the anterior leaflet is called the anterior aspect, while the part attached to the posterior leaflet is called the posterior aspect. The two leaflets are fused at two commissures that are inserted in the annulus just below the level of two cardiac trigones, called the anterolateral trigone and the posterolateral trigone.

In mitral valve repair, coaptation of the posterior and anterior leaflets is important. Also, it is considered important to preserve the normal distance between the two trigones. A significant surgical diminution of the inter-trigonal distance may cause left ventricular outflow obstruction and/or distortion of the base of the aortic valve. Thus, it is desirable to maintain the natural inter-trigonal distance and shape following mitral valve repair surgery.

Mitral valve annulus dilation tends to be confined to the posterior aspect, resulting in a posterior aspect that is larger than normal. Consequently, the repair of mitral valve annulus dilation generally involves reducing the size of the posterior aspect.

In the repair of mitral valve annulus dilation, the associated procedure begins with identification of the trigones. The distance between the trigones (i.e., inter-trigonal distance) or commissures (i.e., inter-commissural distance) remains practically constant during the cardiac cycle in any one particular patient, but may vary from 24 to 40 mm in length in patients. Annuloplasty devices used to treat mitral valve dilation are available in different sizes based upon the distance between the trigones along the anterior aspect (i.e., the aortic curtain). Alternatively, anterior and posterior commissures of the heart are used to size a valve annulus. Either way, it is critical to the successful outcome of the annuloplasty procedure to accurately determine the size of the annulus. Generally, the annuloplasty devices are available in even 2 mm increments from about 24 mm to about 40 mm.

As a part of the mitral valve repair using remodeling, the annulus is generally brought into its shape and positioned such that the inter-trigonal (or inter-commissural) distance is like that at the end of systole. Generally, the involved segment of the annulus, mainly the posterior aspect, is diminished (i.e., constricted) so that the leaflets may coapt correctly on closing, or the annulus is stabilized to prevent post-operative dilatation from occurring. Either result is frequently achieved by the implantation of a prosthetic ring or band in a supra annular position. The purpose of the ring or band is to restrict, remodel and/or support the annulus to correct and/or prevent valvular insufficiency.

Annuloplasty devices for mitral valve repair have generally been configured to restore the original, healthy shape of the mitral annulus at the end of systole. The ring is typically semi-rigid, planar and restores the primary anterior-posterior (A-P) dimension or ratio of the mitral annulus. The ring typically allows for sufficient coaptation of the leaflets at the end of systole.

When annuloplasty devices are used to reduce dilation of the mitral valve and coapt the leaflets, in some cases there is excess leaflet tissue. For example, with Barlow's disease, excess mitral valve leaflet tissue exists. This may result in mitral valve regurgitation. In particular, the anterior mitral leaflet may have excess tissue that, after implantation of the annuloplasty device may experience systolic anterior motion (SAM), which is when the anterior leaflet is pulled into the outflow tract of the left ventricle during the systolic phase of the cardiac cycle. This causes the mitral valve to leak back into the left atrium.

There is a continued desire to be able to improve annuloplasty devices to accommodate different physical structures of the heart due to different disease states of the heart.

SUMMARY OF THE INVENTION

The present invention generally involves a set of devices, a kit, and related methods for the treatment of mitral valve disease. In particular, the kit comprises the set of devices, which comprises annuloplasty devices having a particular size relating to a particular inter-trigonal (or inter-commissural) distance, wherein the set of devices comprises at least two different devices with different anterior-posterior (A-P) ratios, and possibly varying, design, shapes and/or components.

Embodiments of the present invention offer numerous advantages. A single design of annuloplasty device cannot address all the different pathologies or disease states of different mitral valves. Therefore, one advantage of the present invention is that it provides a set of devices that fit a particular size of valve but that that have different designs that address different disease etiologies of the mitral valve. These different designs have varying A-P ratios. Therefore, a surgeon using the present invention will have a choice of different annuloplasty device designs with different A-P ratios available for a particular annuloplasty repair. The devices in the set or kit preferably address most of the pathologies of the mitral valve whether they are congenital, rheumatic, degenerative, or functional, which is beneficial for a surgeon to have at his or her disposal during valve surgery. The set of annuloplasty devices can adjust the A-P ratio of an annulus in order to achieve proper leaflet coaptation, while keeping the inter-trigonal (or inter-commissural) distance intact to preserve both functions of the outflow tract and the aortic valve. Another advantage of the present invention is that the devices in the kit and set preferably have three-dimensional (3D) shape that allows for adequate coaptation and avoids the effect of the area of coaptation being displaced anteriorly with unwanted "acutening" of the mitro-aortic angle that may occur with planar rings. Yet another advantage of the present invention is that the 3D shape of the devices in the kit avoids the need for a surgeon to lower the posterior leaflet, which is a time-consuming procedure. A further advantage is that the set of devices preferably includes devices that have different flexibilities to address different pathologies of the mitral valve, which are readily available to a surgeon. In particular, some of the preferred devices allow flexibility between the trigones of the valve annulus.

A first aspect of the present invention is a kit for annuloplasty repair of a heart valve annulus having an anterior aspect and a posterior aspect. The kit comprises: a plurality of annuloplasty devices each comprising one of a plurality of different sizes; wherein the different sizes each correspond to a different inter-trigonal (or inter-commissural) distance of a heart valve annulus, and for each of the plurality of different sizes there are at least two devices each having the same size but having different A-P ratios. For each size of the plurality of annuloplasty devices, the kit may include three devices that each have different A-P ratios. The three different A-P ratios may be about 0.55, about 0.75 and about 0.85. The devices having the A-P ratios of about 0.75 and about 0.85 may comprise a continuous ring having a saddle shape, an anterior segment that corresponds to the anterior aspect of the annulus and a posterior segment corresponding to the posterior aspect of the annulus, the anterior segment may be flexible, and the posterior segment may be rigid or semi-rigid, and the device having the A-P ratio of about 0.55 may comprise a continuous ring that may be rigid or semi-rigid and may have a saddle shape. The devices having the A-P ratios of about 0.75 and about 0.85 may comprise: an arcuate stiffening element corresponding to the posterior aspect of the valve annulus; and a flexible segment corresponding to the anterior aspect of the valve annulus; wherein the flexible segment is characterized as being more flexible than the stiffening element. The device having the A-P ratio of about 0.55 may comprise: a continuous ring; wherein the ring has an anterior portion that is implanted on the anterior aspect of the mitral valve annulus and a posterior portion that is implanted on the posterior aspect of the mitral valve annulus; the ring is oriented about a central flow axis, the central flow axis defining an upward direction and a downward direction, the downward direction corresponding to the direction of blood flow through the valve annulus; the anterior portion is upwardly curved from a reference plane, which is perpendicular to the central flow axis, by an anterior annular height, which is measured from the reference plane to a point on the anterior portion that is furthest from the reference plane; and the posterior portion is upwardly curved from the reference plane by a posterior annular height, which is measured from the reference plane to a point on the posterior portion that is furthest from the reference plane. The anterior annular height may be greater than the posterior annular height. The ring may have a commissural width, which is defined as the interior distance across the widest part of the ring, and the anterior annular height to commissural width ratio may be greater than the posterior annular height to commissural width ratio. The anterior portion may include a dip inward toward the central flow axis.

A second aspect of the present invention is a set of annuloplasty devices comprising: at least two annuloplasty devices having a particular size that corresponds to an inter-trigonal (or inter-commissural) distance of a heart valve annulus; wherein the at least two annuloplasty devices have different A-P ratios. The at least two annuloplasty devices may have different two-dimensional and/or three-dimensional shapes. The set may include three annuloplasty devices, a first device has an A-P ratio of about 0.55, a second device has an A-P ratio of about 0.75 and a third device has an A-P ratio of about 0.85.

A third aspect of the present invention is a method of choosing an annuloplasty device for implantation in a valve annulus, the method comprising the steps of: measuring the inter-trigonal (or inter-commissural) distance of the valve annulus; providing at least two annuloplasty devices that have a size that corresponds to the measured inter-trigonal distance of the valve annulus, and that each have a different A-P ratio; and choosing one of the at least two annuloplasty devices depending upon the A-P ratio desired. The at least two annuloplasty devices may comprise three annuloplasty devices, a first device has an A-P ratio of about 0.55, a second device has an A-P ratio of about 0.75 and a third device has an A-P ratio of about 0.85. The second and third devices may comprise a continuous ring having a saddle shape, an anterior segment that corresponds to the anterior aspect of the annulus and a posterior segment corresponding to the posterior aspect of the annulus, the anterior segment is flexible, and the posterior segment is rigid or semi-rigid, and the first device comprises a continuous ring that is rigid or semi-rigid and has a saddle shape.

BRIEF DESCRIPTION OF THE DRAWINGS

The present invention will be further explained with reference to the appended Figures, wherein:

FIG. 1 is a plan view of an annuloplasty device of the enlarging category, in accordance with the present invention;

FIG. 2 is a side view of the device in FIG. 1;

FIG. 3 is a plan view of an annuloplasty device of the remodeling category, in accordance with the present invention;

FIG. 4 is a side view of the device in FIG. 3;

FIG. 5 is a plan view of an annuloplasty device of the restrictive category, in accordance with the present invention;

FIG. 6 is a side view of the device in FIG. 5;

DETAILED DESCRIPTION OF PREFERRED EMBODIMENTS

Figure 7:
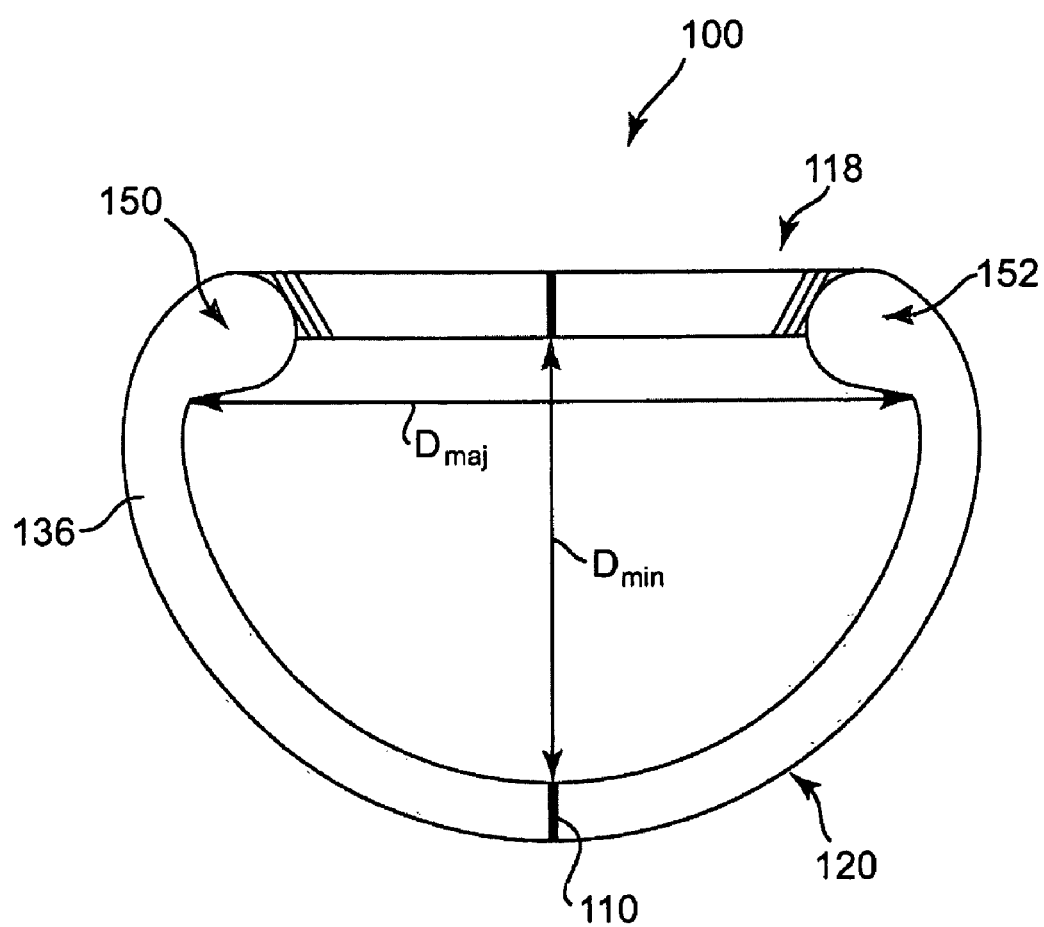
FIG. 7 is a plan view of the device of FIG. 3.
Figure 8:
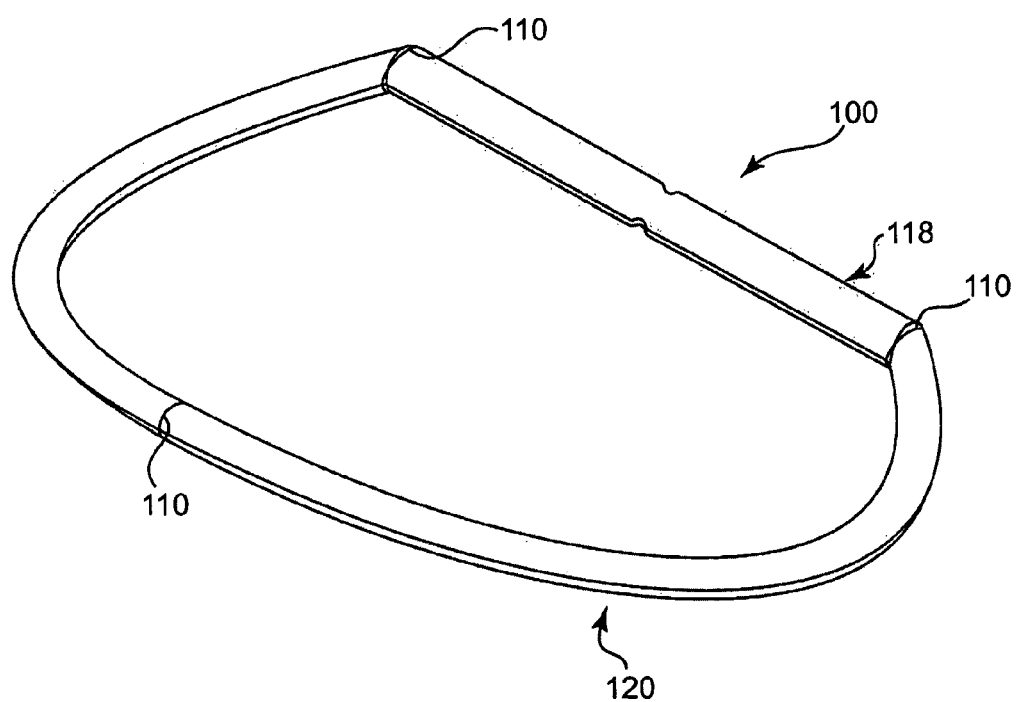
FIG. 8 is a perspective view of the device of FIG. 3.

With reference to the accompanying figures, wherein like components are labeled with like numerals throughout the several figures, a set of, or kit including, annuloplasty devices is disclosed, taught and suggested. In particular, the set of annuloplasty devices correspond to one size of annulus, i.e. one inter-trigonal distance. The set comprises at least two devices of a given size, or inter-trigonal or inter-commissural distance, that have different anterior-posterior (A-P) ratios and possibly different designs. A purpose of the set of devices is to provide a set of devices to a surgeon that are able to address different possible disease etiologies in the repair of a single mitral valve. By allowing a surgeon to choose from a set of at least two annuloplasty devices of a certain size that each have a different A-P ratio, provides the surgeon the ability to more specifically address a problem with a particular valve. The set of annuloplasty devices may also comprise different shapes and/or components that also address different problems with valves.

An exemplary kit and set of annuloplasty devices in accordance with the present invention is shown and described below. However, other kits and sets are also contemplated by the present invention. The exemplary set of devices shown includes three types or categories of annuloplasty devices, with the three types being available in a plurality of different sizes to make up the kit.

FIGS. 1-6 show plan and side views of the three categories of devices in the exemplary set of devices, for comparison purposes. The three categories are described as "enlarging," "remodeling (or restorative)," and "restrictive." FIGS. 1 and 2 show plan and side views of an exemplary annuloplasty device 200 of the enlarging type. FIGS. 3 and 4 show plan and side views of an exemplary annuloplasty device 100 of the remodeling type. And, FIGS. 5 and 6 show plan and side views of an exemplary annuloplasty device 300 of the restrictive type. These devices 100, 200, 300 are, however, exemplary and other designs are also contemplated by the present invention.

As can be seen in FIGS. 1-6, the two-dimensional (2D) and/or the 3D shapes of the three categories of devices 100, 200, 300 preferably differ. The A-P ratios of the categories of devices 100, 200, 300 also differ. The A-P ratio of the device of the remodeling category 100 is preferably that which is considered to be traditional, natural or native to the mitral valve annulus. FIG. 3 demonstrates how the A-P ratio of the devices of the present invention is preferably measured. Device 100 has a major axis diameter $D_{maj}$ (preferably located where the major diameter is the largest) and a minor axis diameter $D_{min}$ (preferably located at the center of the device, or halfway between the parts or the device that correspond to the two trigones of the valve annulus). The ratio of the minor axis (inner) diameter $D_{min}$ to the major axis (inner) diameter $D_{maj}$ is the A-P ratio of the device 100. This is the method used to calculate the A-P ratio for devices of the present invention, although other methods are contemplated.

Another known method for measuring the A-P ratio of a device may alternatively be used to the method described above. This other method, however, results in different A-P ratios for the same device. In general, the A-P ratio calculated using this other method, known as the "centerline method," is about 0.05 higher than for the inner diameter method described above. This centerline method also uses the largest major axis diameter, but takes the measurement from the center of the body of the device on one side to the center of the body of the device on the other side, and does not use the inner diameter. For the minor axis measurement, the distance between the center of the body of the device on one side to the center of the body of the device on the other is measured, which is measured at a centerline located halfway between the parts of the device that correspond to the two trigones of the valve annulus.

A remodeling type of device is shown in FIGS. 3, 4, which is device 100. A preferred embodiment of annuloplasty device 100 is described in a co-pending application, U.S. patent application Ser. No. 11/809,194 and filed May 31, 2007, in the name of Ryan et al., which is incorporated herein by reference in its entirety. FIG. 7 shows another exemplary remodeling type annuloplasty device 100. However, other exemplary remodeling devices having different designs and/or components are also contemplated by the present invention.

As shown in FIG. 7, device 100 preferably includes a member comprising a posterior segment 120 and an anterior segment 118, which correspond to the posterior and anterior aspects of a valve annulus, respectively. The member includes a stiffening element (not shown) in at least its posterior segment 120. A fabric sheath 136 encompasses the stiffening element. In general terms, the stiffening element imparts an arcuate 2D and/or a 3D shape to the annuloplasty ring 100, and is adapted to remodel the valve annulus (not shown) in question to a desired shape and/or size.

The stiffening element (not shown in FIG. 7, but shown in FIG. 9 as 132) is preferably designed to be covered and implanted in a mitral valve annulus. The stiffening element 132 may comprise a metal, ceramic, polymer or a composite, for examples. If the stiffening element 132 comprises a metal wire, the wire can be formed of any medically-acceptable, implantable, biocompatible metal, such as MP35N alloy, titanium, stainless steel, shape memory materials such as Nitinol™, or other similar inert biocompatible metal. Some desirable properties of suitable materials for use in the stiffening element 132 include, but are not limited to, biocompatibility, biostability, and corrosion- and fatigue-resistance.

The stiffening element 132 may be made of a material that imparts rigidity to the stiffening element 132, which in turn imparts rigidity to the annuloplasty device 100. The stiffening element 132 can be made of a material that is suitable for a desired stiffness. In particular, the remodeling device 100 may comprise a semi-rigid material that may optimize and hold the shape of the annulus in place. The stiffening element 132 may, however, comprise a rigid, semi-rigid or flexible material, or may be a combination of rigid, semi-rigid, and/or flexible materials and/or portions. Flexibility or rigidity of the device 100 can vary around its circumference by providing a stiffening element 100 made of multiple materials having different flexibilities/rigidities that are attached or otherwise extend from each other around the circumference of the annuloplasty device 100. The device 100 may provide different grades of flexibility. For example, the device 100 may provide different flexibilities and particularly to the part of the device 100 that corresponds to the inter-trigonal area, or anterior aspect, of the annulus.

The stiffening element 132 may generally have a circular square cross section. However, cross sections of other shapes are also contemplated by the present invention (e.g., square, square circular, circular, rectangular, elliptical, triangular, or the like). Different cross-sectional shapes can be used to impart varying degrees of bending or torsional stiffness depending on the bending/twisting plane with respect to a section modulus. Also, the cross-sectional shape may be varied around the circumference of the stiffening element 132. An annuloplasty device 100 having varying rigidity can be made, for example, by providing a stiffening element that varies in area and/or cross-section around its circumference, thereby providing a ring having varying flexibility around its circumference.

Preferably, the stiffening element 132 may be covered or over molded with a biocompatible, biostable, implantable medical grade elastomeric protective coating. The coating may comprise an elastomeric thermoplastic polymer (e.g., polyurethane) or a silicone (e.g., liquid silicone rubber) to provide a consistent profile and to create desirable needle penetration properties for the surgeon. Also, the protective coating can optionally impart radiopaque and echogenic in vivo visualization, for example. Alternatively, the protective coating may be tubing within which the stiffening element is disposed, with the tubing consisting of biocompatible, biostable, implantable medical grade elastomeric material, such as elastomeric thermoplastic polymer (e.g., polyurethane) or silicone. The some embodiments, the protective coating or tubing may comprise varying profiles to create desirable needle penetration into the device for a surgeon. In yet other embodiments, the protective coating may be eliminated.

The stiffening element 132, with or without the protective coating, is preferably covered with a sheath or covering 136. The covering or sheath 136 may comprise a knitted polymeric fabric (e.g., Dacron™), although woven, non-woven materials (e.g., spun-bond, melt-blown, staple fiber matrix, etc.), braided fabrics, or metallic braids (e.g. titanium, Nitinol™, and stainless steel wires) are also contemplated, as well as sheaths formed of harvested biological tissue (e.g., pericardial tissue). The covering or sheath 136 may optionally be provided with any of various biocompatible coatings. The preferred purpose of the covering or sheath 136 is to provide a site for attachment of the device 100 to an annulus using invasive or minimally invasive surgical techniques as well as to allow for in-growth of the device 100 with the native valve tissue. A plurality of knotted sutures is typically used to secure the annuloplasty device 100 to the mitral valve annulus, although other fasteners such as staples, fibrin glue, or the like may be used.

The stiffening element 132 may also be radiopaque, echogenic, MRI-compatible and/or otherwise imaging enhanced so that it may readily be visualized after implantation using various existing techniques or any future developed techniques, including x-ray, MRI, echogram, etc. By "radiopaque," it is meant that the material or element prevents the passage of radiation. "Radiation" is meant to include electromagnetic energy, light, etc. By "echogenic," it is meant that it reflects sound waves. By "MRI-compatible" it is meant that the material or element is both MRI safe and capable of being excited by MRI.

Figure 9:
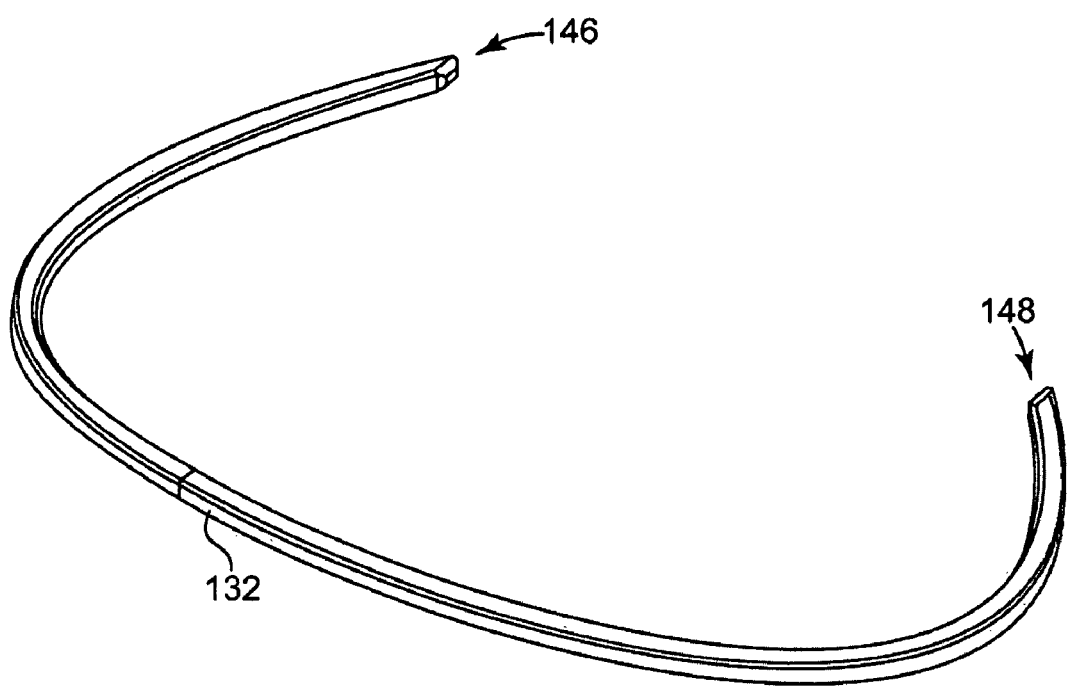
FIG. 9 is a perspective view of the stiffening element of the device of FIG. 3 as shown in FIG. 8.

For the remodeling category, the device 100 preferably includes the stiffening element 132 only in the portion of the device 100 that corresponds to the posterior leaflet of the mitral valve annulus. The stiffening element 132 defines discrete, first and second ends 146, 148 (FIG. 9). Preferably, the anterior segment 118 of the device 100 includes a flexible configuration that is characterized as being more flexible than the stiffening element 132.

Available shapes for the stiffening element 132 are described in greater detail below. In general terms, however, for the remodeling category of devices, the stiffening element 132 is preferably shaped to match the native or natural shape of a valve annulus in which an annuloplasty device 100 is to be applied at least with respect to the desired size of a modified or corrected annulus or portion thereof. Thus, the stiffening element 132 can be generally shaped to mimic the native natural mitral valve posterior annulus anatomy (i.e., generally symmetrical, horseshoe-like shape) for mitral valve annulus repair.

The flexible anterior segment 118 may comprise a plurality of fabric layers, which may have varied stiffnesses. Alternatively, the anterior segment 118 may comprise silicone, which may be molded extruded or cast. Another exemplary configuration is to include one or more polymer strips inside a fabric covering. Other flexible configurations for the anterior segment 118 are also contemplated.

Flexibility of the anterior segment 118 is important to address issues associated with some disease etiologies of heart valves. For example, the flexible anterior segment 118 may allow excess anterior leaflet tissue to move or flex within the ventricular outflow tract.

The fabric sheath 136 of device 100 is preferably formed about the stiffening element 132 for all three types of rings. The fabric sheath may comprise a knitted polyester fabric (e.g., Dacron™), although woven, non-woven (e.g., spun-bond, melt-blown, staple fiber matrix, etc.) or braided fabrics are also contemplated, as well as sheaths formed of harvested biological tissue (e.g., pericardial tissue). The fabric sheath 136 may optionally be provided with any of various biocompatible coatings.

The fabric sheath preferably includes three sutures 110 that mark certain areas for implantation purposes. There are two suture marks on the anterior portion 118 that correspond to where the device 100 is designed to be secured to the antero-lateral and the postero-medial trigones of the annulus. Another suture mark 110 identifies a midpoint of the posterior segment 120 of the device 100. Similar suture marks 210, 310 are also found on devices 200 and 300, respectively.

The orientation of device 100 to a mitral valve annulus is specific. The annuloplasty device 100 includes a posterior segment 120 and an anterior segment 118 that make up the circumference of the device 100. The posterior segment 120 corresponds with a posterior aspect of a mitral valve annulus, and is defined along a region of the stiffening element 132. The anterior segment 118 corresponds with an anterior aspect of a mitral valve annulus. As such, upon final implant, the posterior segment 120 of the annuloplasty device 100, and in particular the stiffening element 132 associated therewith, serves to rigidly or semi-rigidly remodel a shape of the posterior aspect to a desired extent. Conversely, the anterior segment 118 may flex or move with natural movement of the anterior aspect, and impedes overt dilatation of the anterior aspect by limiting separation of stiffening element 132 ends 146, 148. In other embodiments, the anterior segment 118 of the annuloplasty device 100 can have a slightly more rigid configuration. With this alternative configuration, the anterior segment 118 is still capable of moving with natural movement of the anterior aspect and impedes overt dilatation of the annuloplasty device 100, and in particular the stiffening element 132, when in a taut state.

Lateral spacing (indicated as "$L_s$" in FIGS. 10, 11) between the first and second free ends 146, 148 of the stiffening element 132 in device 100 and the first and second free ends 246, 248 of the stiffening element in device 200 may be varied. For example, some preferred lateral spacings are 0.55 in (15.24 mm), 0.8 in (20.32 mm) and 1.0 in (25.4 mm), for a device 100 having a $D_{maj}$ of 32 mm. For the same size (i.e., $D_{maj}$ of 32 mm) of enlarging device 200, some preferred lateral spacings are 0.9 in (22.86 mm) and 1.13 in (28.7 mm).

The remodeling device 100 and the enlarging device 200 (FIGS. 1, 2) are preferably generally similar in construction. Therefore, the description above with regard to the components of device 100 also preferably applies to enlarging device 200. One preferred difference between the two devices, however, is that the anterior segment 218 of the enlarging type device 200 is preferably fully flexible. The flexible anterior segment 218 of device 200 is particularly well suited to address Barlow's disease and the resultant SAM of the anterior leaflet. The flexible anterior segment 218 of device 200 allows the excess anterior leaflet tissue to move or flex within the ventricular outflow tract, which preserves the ventricular outflow tract. The anterior segment 118 of the remodeling type device 100 is, however, preferably less flexible and preferably made with a stiffer fabric or other material than that of the enlarging type device 200.

Similar to remodeling device 100, enlarging device 200 includes an anterior segment 218 and a posterior segment 220 that make up the circumference of the device 200. Another difference between enlarging device 200 and remodeling device 100 is that the posterior segment 220 of the enlarging device 200 is larger or longer than the posterior segment 120 of the remodeling device 100. As a result, the A-P ratio of the enlarging device 200 is preferably larger than that of the remodeling device 100, and most preferably about 0.85. The preferred A-P ratio of the remodeling device of the present invention is about 0.55 to about 0.7.

Preferably, all three categories of devices 100, 200, 300 have a non-planar or 3D shape that mimics or matches the native, natural mitral valve annulus while in a particular portion of the cardiac cycle. Preferably, the 3D shapes of the remodeling device 100 and enlarging device 200 are similar. Exemplary preferred 3D shapes can be seen in the perspective views of the devices 100, 200, 300 in FIGS. 15, 14, 16, respectively.

Figure 14:
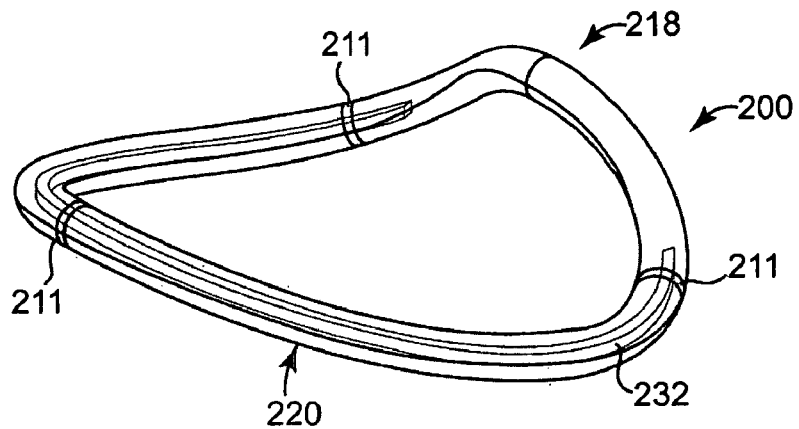
FIG. 14 is a see-through, perspective view of the device of FIGS. 1 and 2.
Figure 15:
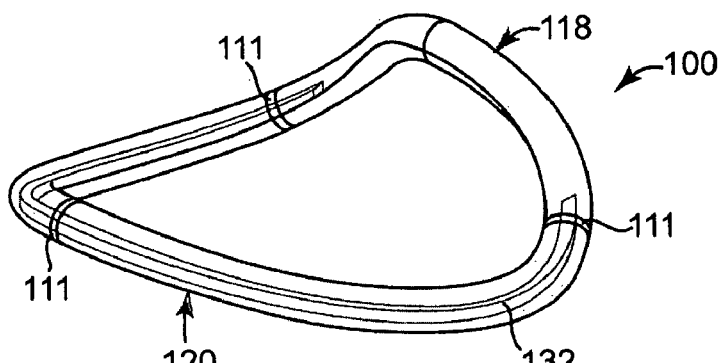
FIG. 15 is a see-through, perspective view of the device of FIGS. 3 and 4.
Figure 16:
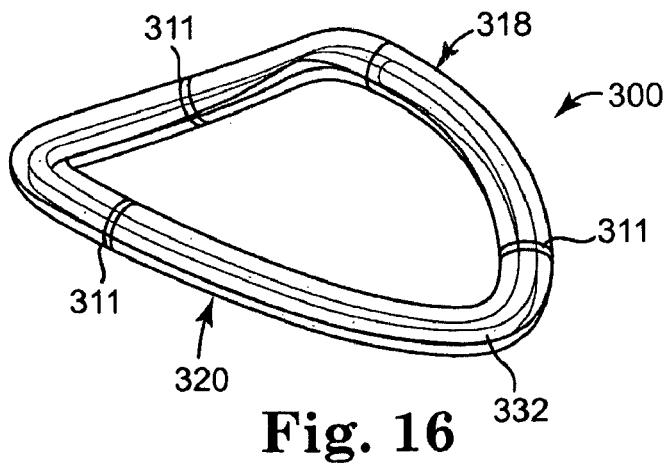
FIG. 16 is a see-through, perspective view of the device of FIGS. 5 and 6.

As FIGS. 14, 15 illustrate, the anterior segments 218, 118 of devices 200, 100 are preferably flexible and may be contoured in various geometries by elastomeric properties of the anterior segments 218, 118 itself or from the device holder. The flexible anterior segments 218, 118 may be contoured like that of the restrictive device 300, which mimics the annulus, or may the anterior segments 218, 118 may simply close the gap between the stiffening elements ends 246 and 248 or 146 and 148 in the shortest manner possible.

Due to the flexibility of the anterior segment 118 in remodeling device 100 and the anterior segment 218 in enlarging device 200, the anterior segment may move inward toward the center or outward away from the center of such devices. As a result, the minor diameter may be reduced or increased, which affects the calculation of the A-P ratio of the devices.

FIG. 9 shows only the stiffening element 132 of device 100. The stiffening element 132 of the device may define a compound 2D curve as shown or as described in U.S. Pat. No. 6,786,924. Further, and with reference to FIG. 9, the stiffening element 132 can be generally saddle-shaped. The level or severity of the saddle shape can be selected as desired. In some embodiments, for example, a saddle shape defined by the stiffening element 132 may approximate the variations in height evidenced or experienced by the posterior aspect of a healthy mitral valve annulus in a systolic state or a diastolic state as described, for example, in Thomasz, A. T., et al., *Annular Height-to-Commissural Width Ratio of Annuloplasty Rings In Vivo*, (Circulation, 2005; 112 ([Suppl. I]:I-423-428), the teachings of which are incorporated herein by reference. The 3D shape shown and described herein are preferred, however other shapes are also contemplated by the present invention.

Figure 10:
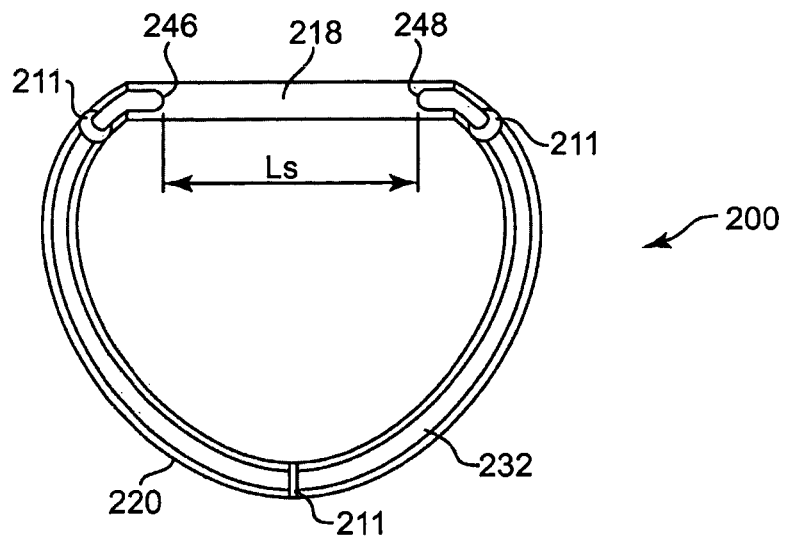
FIG. 10 is a plan view of the device of FIG. 1, with portions cut away.
Figure 11:
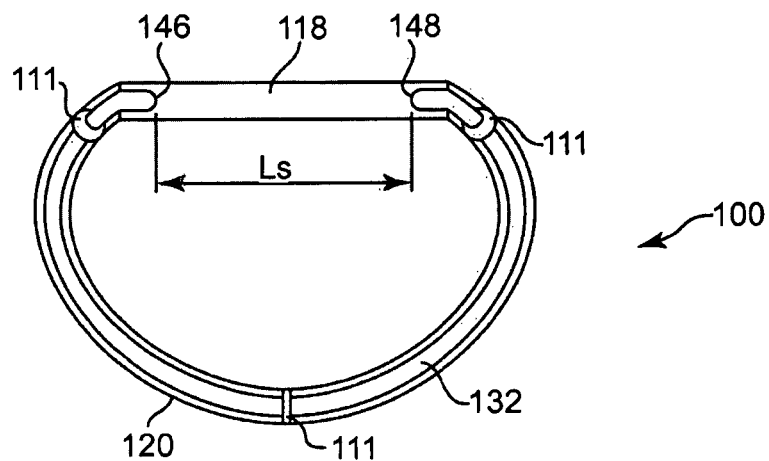
FIG. 11 is a plan view of the device of FIG. 3, with portions cut away.
Figure 12:
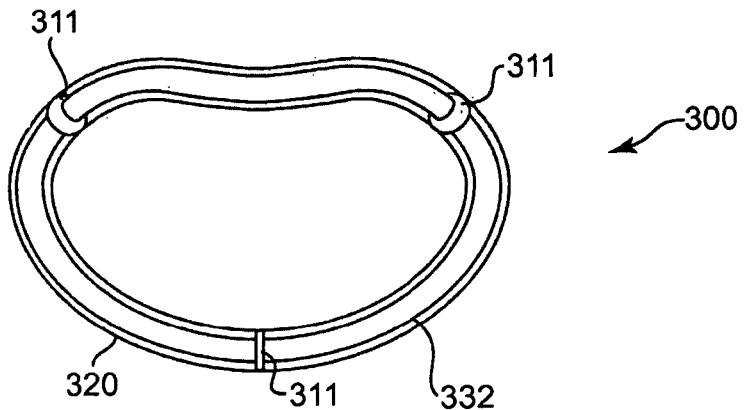
FIG. 12 is a plan view of the device of FIG. 5, with portions cut away.

Although the remodeling device 100 (FIGS. 3, 4) and the enlarging device 200 (FIGS. 1, 2) are preferably similar in construction, the restrictive device 300, as shown in FIGS. 5 and 6, is preferably different in construction from the other devices 100, 200. Although many components are preferably the same as that described above for devices 100 and 200, in the exemplary restrictive device 300 rather than having a discontinuous stiffening element, the device 300 has a continuous stiffening element 332. FIGS. 10-12 show the three devices 100, 200, 300 in cut-away view. FIG. 10-12 shows cut-away views of enlarging device 200, remodeling device 100 and restrictive device 300, respectively. In particular, these figures show the preferred stiffening elements 232, 132, 332 of devices 200, 100, 300, respectively. As shown, the stiffening elements 132, 232 of devices 100, 200 are preferably discontinuous, while the stiffening element 332 of the restrictive device 300 is preferably continuous.

FIGS. 10-12 also show the inclusion of optional radiographic markers 211, 111, 311 in the devices 200, 100, 300, respectively. The markers 211, 111, 311 may comprise any material that allows them to be visualized during or after implantation using various existing techniques or any future developed techniques, such as, e.g., x-ray. The markers 211, 111, 311 may assist a surgeon in correctly placing the devices 200, 100, 300 during implantation.

As described above, many of the components of the restrictive device 300 are similar to those in the remodeling device 100. One preferred difference is that the stiffening element 332 of the restrictive device 300 is continuous. The restrictive device 300 is also preferably a fully rigid ring. Such a configuration is preferably desired in order to obtain good coaptation of valve leaflets and ensure a restrictive result in dilated cardiomyopathy with tethered valve leaflets.

The 2D and 3D shapes of the restrictive device 300 also preferably differ from the remodeling 100 and enlarging 200 devices. For instance, the 2D shape of the restrictive device 300 is different, as shown in FIG. 5. In particular, the anterior segment 318 of the device 300 includes a scallop or dip 344 when viewed from a top or planar view. The scallop or dip 344 is a contoured area that curves toward the center, open area, or central flow axis of the device 300. The inward scallop or dip 344 of the anterior portion 318 effectively reduces the distance between the anterior portion 318 and the posterior portion 320 across a portion of the width of the device 300 (i.e., reduces the A-P ratio), while maintaining a relatively large effective orifice area, which can be used to restore valvular competency. The A-P ratio of the restrictive device 300 is preferably about 0.55. The scallop or dip 344 may act to reduce stress on the leaflets and/or annulus. Additionally, the scallop or dip 344 may allow for anatomic remodeling to preserve aortic valve function.

Due to the inward scallop or dip 344 in remodeling device 300, the inner diameter of the device in a direction of the minor axis varies. If the measurement of the minor diameter is taken from the centerline of the device (i.e., halfway between parts corresponding to the trigones), the minor axis diameter will be less than if the measurement is taken at other locations.

Figure 13:
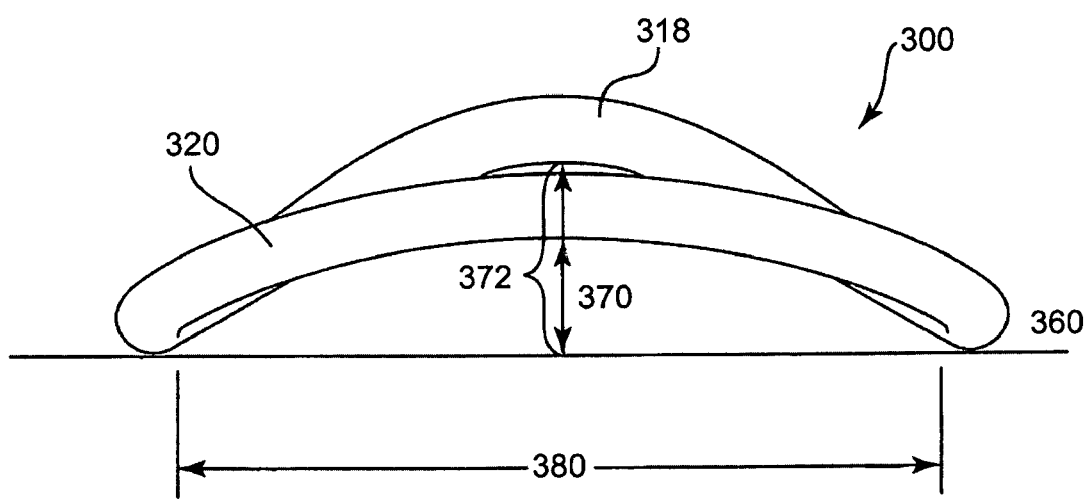
FIG. 13 is a rear view of the device of FIGS. 5 and 6.

FIG. 13 shows a rear view of restrictive device 300. The posterior segment 320 is curved upwardly from a reference plane 360 by a posterior annular height 370. The anterior segment 318 is also curved upwardly from the reference plane 360 by an anterior annular height 372. For comparison, both of these heights are generally measured at approximately the same position across the width of the device 300 and are mainly referred to herein as the points where the heights are the largest (i.e., where the posterior 320 and anterior 318 segments are the furthest from reference plane 360).

FIG. 13 shows that the posterior annular height 370 is preferably different from the anterior annular height 372, thereby creating a shape that can be considered to be asymmetrical. Also, the curvature of the posterior segment 320 is different from the curvature of the anterior segment 318 across at least most of the width of the device 300. Preferably, the anterior annular height 372 is greater than the posterior annular height 370, which is designed to correspond with the general shape of the human anatomy, particularly the relationship between the anterior and posterior annulus.

FIG. 13 show a commissural width 380 of device 300 which is the interior distance across the widest part of the device 300. The anterior annular height 372 divided by the commissural width (at approximately 380) provides an annular height to commissural width ratio of the anterior segment 318 of the device 300, which is referred to herein as "$AHCWR_{ANT}$", Similarly, the posterior annular height 370 divided by the commissural width 380 provides an annular height to commissural width ratio of the posterior portion 320 of ring 300 referred to herein as "$AHCWR_{POST}$". These ratios of anterior or posterior annular height to commissural width ratios normalize the saddle-shaped vertical component of the device 300 throughout varying valve sizes. The $AHCWR_{ANT}$ is different from the $AHCWR_{POST}$, since the preferred restrictive device 300 is asymmetrical relative to its posterior and anterior portions. Further, because anterior annular height is larger than posterior annular height in order to model the annular anatomy of the patient, $AHCWR_{ANT}$ is larger than $AHCWR_{POST}$. The preferred device 300 has an $AHCWR_{ANT}$ of 25% and an $AHCWR_{POST}$ of 15%, although other percentages are also contemplated.

Preferably, the restrictive device 300 is fully rigid. Preferably, the stiffening element 332 of device 300 comprises a material such as titanium. Also, preferably, the cross-section of the stiffening element 332 is the same throughout and thereby provides uniform rigidity throughout. Other configurations are contemplated, however.

The set of devices of the present invention may preferably be available in many different sizes, which is provided as a kit. The size of the devices is based upon the length of the major axis of the device, which is $D_{maj}$, as indicated in FIG. 1, which correlates to the inter-trigonal (or inter-commissural) distance of an annulus. Annuloplasty devices are generally available starting with a $D_{maj}$ of 24 mm and increasing by 2 mm each. Therefore, the annuloplasty devices, 100, 200 and 300 of the present invention are preferably available having a $D_{maj}$ of about 24 mm to about 40 mm. Most preferably, at least three of the most common sizes are available, which are 28 mm, 32 mm and 36 mm.

For each size, $D_{maj}$, or inter-trigonal (or inter-commissural) distance, of device there are three types or categories, as discussed above. The three different categories of devices are designed to address different problems, pathologies, disease states, etc., relating to the heart. The remodeling (restorative) category has a traditional annuloplasty device design, which reshapes the annulus that generally has a dilated posterior annulus. The remodeling (restorative) category of devices is designed to address degenerative heart disease, myxomatous degeneration, fibroelastic deficiency, types I and II IMR, and degenerative diseases which result in a dilated posterior annulus, for examples. In particular, the restrictive category of devices is preferably designed to address cardiac ischemia, dilated cardiomyopathy, tethered leaflets in secondary mitral valve insufficiency, and Type IIIb IMR, for examples. And, the enlarging category of devices is desired to address Barlow's syndrome, systolic anterior motion (SAM) in Myxoid Heart Disease, septal hypertrophy, and Type II IMR, for examples. It is contemplated, however, that the set of devices may include additional types of devices that address additional heart conditions.

Although the present invention has been described above with regard to a set of three annuloplasty devices of varying A-P ratios, but have the same size, other sets of devices are also contemplated. For example, more than three devices with additional A-P ratios may be included in the set and kit. Also, other shapes and designs of devices may be included that would provide desired A-P ratios in the set and kit.

The present invention also includes methods that relate to the set and kit of annuloplasty devices. One method is a method of choosing an annuloplasty device for implantation in a valve annulus, the method comprising the steps of: measuring the inter-trigonal distance of the valve annulus; providing at least two annuloplasty devices that have a size that corresponds to the measured inter-trigonal distance of the valve annulus, and that each have a different A-P ratio; and choosing one of the at least two annuloplasty devices depending upon the A-P ratio desired. Other similar methods are also contemplated by the present invention.

The present invention as shown in the accompanying figures and described herein is particularly designed for or relates to the mitral valve. However, the present invention is not limited for application to the mitral valve, and it is contemplated that variations of the embodiments may apply to other valves.

It is to be understood that while particular embodiments of the present inventive annuloplasty device have been illustrated for use in typical valve repair procedures, various modifications to shape, and arrangement of parts can be made as may be desirable for varying applications as may relate to valve sizes, disease states, or later developed techniques. The present invention has now been described with reference to several embodiments thereof. The entire disclosure of any article, patent or patent application identified herein is hereby incorporated by reference. The foregoing detailed description has been given for clarity of understanding only. No unnecessary limitations are to be understood therefrom. It will be apparent to those skilled in the art that many changes can be made in the embodiments described without departing from the scope of the invention.

The invention claimed is:

1. A kit for annuloplasty repair of a heart valve annulus having an anterior aspect and a posterior aspect, the kit comprising:
a plurality of prosthetic annuloplasty devices from which a device can be selected for implantation along a heart valve annulus for remodeling, enlarging or restricting the heart valve annulus, the plurality of annuloplasty devices comprising a plurality of annuloplasty devices of different sizes; wherein the different sizes each correspond to a different inter-trigonal or inter-commissural distance of a heart valve annulus, and the kit also including a plurality of annuloplasty devices of the same size but having different anterior-posterior ratios with one annuloplasty device of one size with an anterior-posterior ratio for enlarging or restricting the heart valve annulus in addition to another annuloplasty device of the same size for remodeling the heart valve annulus at a normal anterior-posterior ratio, wherein the devices having different anterior-posterior ratios comprises of a continuous ring having a saddle shape.

2. The kit of claim 1, wherein for each size of the plurality of annuloplasty devices, the kit includes three devices of the same size that each have different anterior-posterior ratios.

3. The kit of claim 2, wherein the three different anterior-posterior ratios are about 0.55, about 0.75 and about 0.85.

4. The kit of claim 3, wherein the devices having the anterior-posterior ratios of about 0.75 and about 0.85 comprise a continuous ring having a saddle shape, an anterior segment that corresponds to the anterior aspect of the annulus and a posterior segment corresponding to the posterior aspect of the annulus, the anterior segment is flexible, and the posterior segment is rigid or semi-rigid, and the device having the anterior-posterior ratio of about 0.55 comprises a continuous ring that is rigid or semi-rigid and has a saddle shape.

5. The kit of claim 3, wherein the device having the anterior-posterior ration of about 0.75 and about 0.85 comprises:
an arcuate stiffening element corresponding to the posterior aspect of the valve annulus; and
a flexible segment corresponding to the anterior aspect of the valve annulus; wherein the flexible segment is characterized as being more flexible than the stiffening element.

6. The kit of claim 3, wherein the device having the anterior-posterior ratio of about 0.55 comprises:
a continuous ring;
wherein the ring has an anterior portion that is implanted on the anterior aspect of the mitral valve annulus and a posterior portion that is implanted on the posterior aspect of the mitral valve annulus;
the ring is oriented about a central flow axis, the central flow axis defining an upward direction and a downward direction, the downward direction corresponding to the direction of blood flow through the valve annulus;
the anterior portion is upwardly curved from a reference plane, which is perpendicular to the central flow axis, by an anterior annular height, which is measured from the reference plane to a point on the anterior portion that is furthest from the reference plane; and
the posterior portion is upwardly curved from the reference plane by a posterior annular height, which is measured from the reference plane to a point on the posterior portion that is furthest from the reference plane.

7. The kit of claim 6, wherein the anterior annular height of the device having the anterior-posterior ratio of about 0.55 is greater than the posterior annular height of the device.

8. The kit of claim 6, wherein the device having the anterior-posterior ratio of about 0.55 has a commissural width, which is defined as the interior distance across the widest part of the ring, and the anterior annular height to commissural width ratio is greater than the posterior annular height to commissural width ratio.

9. The kit of claim 6, wherein the anterior portion of the device having the anterior-posterior ratio of about 0.55 includes a dip inward toward the central flow axis.

* * * * *